United States Patent
Middleton

(10) Patent No.: US 9,735,370 B2
(45) Date of Patent: Aug. 15, 2017

(54) COMPOUND, DEVICE AND METHOD OF MAKING SAME

(71) Applicants: CAMBRIDGE DISPLAY TECHNOLOGY LIMITED, Cambridgeshire (GB); SUMITOMO CHEMICAL COMPANY LIMITED, Tokyo (JP)

(72) Inventor: Helen Middleton, Nottingham (GB)

(73) Assignees: CAMBRIDGE DISPLAY TECHNOLOGY LIMITED, Cambridgeshire (GB); SUMITOMO CHEMICAL COMPANY LIMITED, Tokyo (JP)

(*) Notice: Subject to any disclaimer, the term of this patent is extended or adjusted under 35 U.S.C. 154(b) by 452 days.

(21) Appl. No.: 14/355,572

(22) PCT Filed: Oct. 30, 2012

(86) PCT No.: PCT/GB2012/000818
§ 371 (c)(1),
(2) Date: Apr. 30, 2014

(87) PCT Pub. No.: WO2013/064793
PCT Pub. Date: May 10, 2013

(65) Prior Publication Data
US 2014/0299868 A1   Oct. 9, 2014

(30) Foreign Application Priority Data

Nov. 2, 2011  (GB) .................................. 1118940.4
Nov. 2, 2011  (GB) .................................. 1118941.2

(51) Int. Cl.
*H01L 51/00* (2006.01)
*C09K 11/06* (2006.01)
(Continued)

(52) U.S. Cl.
CPC ........ *H01L 51/0069* (2013.01); *C07D 265/38* (2013.01); *C09B 19/00* (2013.01);
(Continued)

(58) Field of Classification Search
None
See application file for complete search history.

(56) References Cited

U.S. PATENT DOCUMENTS 4,539,507 A   9/1985   VanSlyke et al.
5,723,873 A   3/1998   Yang
(Continued)

FOREIGN PATENT DOCUMENTS

CN   101294004 A   10/2008
EP   0 562 883 A2   9/1993
(Continued)

OTHER PUBLICATIONS

Machine English translation of Yokoyama et al. (JP 2011-178742 A). Jul. 6, 2016.*
(Continued)

*Primary Examiner* — J. L. Yang
(74) *Attorney, Agent, or Firm* — Marshall, Gerstein & Borun LLP

(57) ABSTRACT

An organic light-emitting device comprises an anode, a cathode and a light-emitting layer between the anode and the cathode. The light-emitting layer comprises a compound of formula (I):

(Continued)

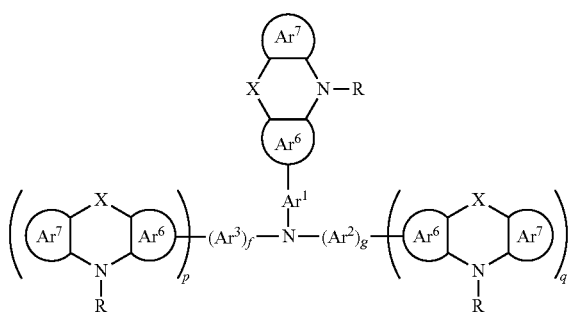

(I)

wherein $Ar^1$, $Ar^2$, $Ar^3$, $Ar^6$ and $Ar^7$ in each occurrence independently represent an unsubstituted or substituted aryl or heteroaryl group; X independently in each occurrence represents S or O; R independently in each occurrence represents H or a substituent; p is 0 or 1; q is 0 or 1; f is 1, 2 or 3; g is 1, 2 or 3; and adjacent groups $Ar^3$ or adjacent groups $Ar^2$ may be linked by a divalent group to form a ring. This compound can provide a bluer emitter that can be blended into current host formulations (deep blue, CIEy<0.08) suitable for solution processing.

13 Claims, 2 Drawing Sheets

(51) Int. Cl.

| | |
|---|---|
| H05B 33/14 | (2006.01) |
| C07D 265/38 | (2006.01) |
| H01L 51/56 | (2006.01) |
| C09B 19/00 | (2006.01) |
| C09B 57/00 | (2006.01) |
| H01L 51/50 | (2006.01) |

(52) U.S. Cl.
CPC ............ *C09B 57/008* (2013.01); *C09K 11/06* (2013.01); *H01L 51/0003* (2013.01); *H01L 51/0061* (2013.01); *H01L 51/0067* (2013.01); *H01L 51/0071* (2013.01); *H01L 51/0072* (2013.01); *H01L 51/5036* (2013.01); *H01L 51/56* (2013.01); *H05B 33/14* (2013.01); *C09K 2211/1007* (2013.01); *C09K 2211/1014* (2013.01); *C09K 2211/1033* (2013.01); *H01L 51/5012* (2013.01)

(56) References Cited

U.S. PATENT DOCUMENTS

| | | | |
|---|---|---|---|
| 5,798,170 | A | 8/1998 | Zhang et al. |
| 6,268,695 | B1 | 7/2001 | Affinito |
| 6,953,628 | B2 | 10/2005 | Kamatani et al. |
| 7,030,138 | B2 | 4/2006 | Fujimoto et al. |
| 7,125,998 | B2 | 10/2006 | Stossel et al. |
| 7,527,879 | B2 | 5/2009 | Kamatani et al. |
| 2002/0117662 | A1 | 8/2002 | Nii |
| 2002/0182441 | A1 | 12/2002 | Lamansky et al. |
| 2004/0127666 | A1 | 7/2004 | Inbasekaran et al. |
| 2004/0151829 | A1* | 8/2004 | Boroson ............ H01L 27/3211 427/64 |
| 2005/0186444 | A1 | 8/2005 | Zheng et al. |
| 2007/0176148 | A1* | 8/2007 | Park ........................ C09K 11/06 252/301.16 |
| 2009/0066235 | A1 | 3/2009 | Yabunouchi et al. |
| 2011/0175069 | A1 | 7/2011 | Son et al. |

FOREIGN PATENT DOCUMENTS

| | | |
|---|---|---|
| EP | 0 707 020 A2 | 4/1996 |
| EP | 0 880 303 A1 | 11/1998 |
| EP | 0 901 176 A2 | 3/1999 |
| EP | 0 947 123 A1 | 10/1999 |
| EP | 0 949 850 A1 | 10/1999 |
| EP | 1 245 659 | 10/2002 |
| EP | 2 048 176 A1 | 4/2009 |
| EP | 0 842 208 B2 | 8/2009 |
| EP | 2 216 356 A1 | 8/2010 |
| GB | 2 348 316 A | 9/2000 |
| JP | 2002-324679 A | 11/2002 |
| JP | 2007-031704 A | 2/2007 |
| JP | 2010-238937 A | 10/2010 |
| JP | 2011178742 A * | 9/2011 |
| WO | WO-90/13148 A1 | 11/1990 |
| WO | WO-98/10621 A1 | 3/1998 |
| WO | WO-98/57381 A1 | 12/1998 |
| WO | WO-99/54385 A1 | 10/1999 |
| WO | WO-00/48258 A1 | 8/2000 |
| WO | WO-00/53656 A1 | 9/2000 |
| WO | WO-01/19142 A1 | 3/2001 |
| WO | WO-01/81649 A1 | 11/2001 |
| WO | WO-02/44189 A1 | 6/2002 |
| WO | WO-02/45466 A1 | 6/2002 |
| WO | WO-02/066552 A1 | 8/2002 |
| WO | WO-02/068435 A1 | 9/2002 |
| WO | WO-02/081448 A1 | 10/2002 |
| WO | WO-02/084759 A1 | 10/2002 |
| WO | WO-2004/060970 A1 | 7/2004 |
| WO | WO-2008/003604 A2 | 1/2008 |
| WO | WO-2010/065178 A1 | 6/2010 |

OTHER PUBLICATIONS

Kim et al. (Mol. Cryst. Liq. Cryst. 2007, 407, p. 231). Jul. 6, 2016.*
Bernius et al., "Progress with Light-Emitting Polymers", *Adv. Mater.*, 12(23):1737-1750 (2000).
Li et al., "Design and Synthesis of Solution Processable Small Molecules Towards High Photovoltaic Performance," *J. Mater. Chem.*, 21:2159-2168 (2011).
Michaelson, "The work function of the elements and its periodicity", *J. Applied Physics*, 48(11): 4729-4733 (1977).
Niu et al., "Thermal Annealing Below the Glass Transition Temperature: A General Way to Increase Performance of Light-Emitting Diodes Based on Copolyfluorenes," *Appl. Phys. Lett.*, 81(4):634-636 (2002).
Setayesh et al., "Bridging the Gap Between Polyfluorene and Ladder-Poly-p-phenylene: Synthesis and Characterization of Poly-2,8-indenofluorene," *Macromolecules*, 33(6):2016-2020 (2000).
Tokito et al., "Metal oxides as a hole-injecting layer for an organic electroluminescent device", *J. Phys. D: Appl. Phys.*, 29:2750-2753 (1996).
Yamaguchi et al., "Effects of B and C on the Ordering of L1$_0$-CoPt Thin Films," *Appl. Phys. Lett.*, 79(5):2001-2003 (2001).
Yamamoto, "Electrically Conducting and Thermally Stable π-Conjugated Poly(Arylene)s Prepared by Organometallic Processes," *Prog. Polym. Sci.*, 17:1153-1205 (1993).
Yang et al., "Efficient blue polymer light-emitting diodes from a series of soluble poly(paraphenylene)s", *J. Appl. Phys.*, 79(2):934-939 (1996).
Combined Search and Examination Report for Application No. GB1118940.4, dated Feb. 24, 2012.
International Preliminary Report on Patentability for Application No. PCT/GB2012/000818, dated May 6, 2014.
International Search Report and Written Opinion for Application No. PCT/GB2012/000818, dated Jan. 28, 2013.

* cited by examiner

COMPOUND, DEVICE AND METHOD OF MAKING SAME

SUMMARY OF THE INVENTION

This invention relates to a compound, organic light emitting devices comprising the compound, compositions containing the compound and methods of making said compound and devices.

BACKGROUND OF THE INVENTION

Electronic devices comprising active organic materials are attracting increasing attention for use in devices such as organic light emitting diodes, organic photovoltaic devices, organic photosensors, organic transistors and memory array devices. Devices comprising organic materials offer benefits such as low weight, low power consumption and flexibility. Moreover, use of soluble organic materials allows use of solution processing in device manufacture, for example inkjet printing or spin-coating.

A typical organic light-emissive device ("OLED") is fabricated on a glass or plastic substrate coated with a transparent anode such as indium-tin-oxide ("ITO"). A layer of a thin film of at least one electroluminescent organic material is provided over the first electrode. Finally, a cathode is provided over the layer of electroluminescent organic material. Charge transporting, charge injecting or charge blocking layers may be provided between the anode and the light-emitting layer and/or between the cathode and the light-emitting layer.

In operation, holes are injected into the device through the anode and electrons are injected into the device through the cathode. The holes and electrons combine in the organic light-emitting layer to form excitons which then undergo radiative decay to give light.

In WO90/13148 the organic light-emissive material is a conjugated polymer such as poly(phenylenevinylene). In U.S. Pat. No. 4,539,507 the organic light-emissive material is of the class known as small molecule materials, such as tris-(8-hydroxyquinoline) aluminium ("Alq$_3$").

EP 2216356 discloses polymers comprising fluorene repeat units with triphenylamine repeat units pendant from the fluorene units.

Polymers comprising triarylamine repeat units are disclosed in WO 99/54385.

Polymers comprising phenoxazine repeat units are disclosed in WO 2004/060970.

SUMMARY OF THE INVENTION

In a first aspect, the invention provides a compound of formula (I):

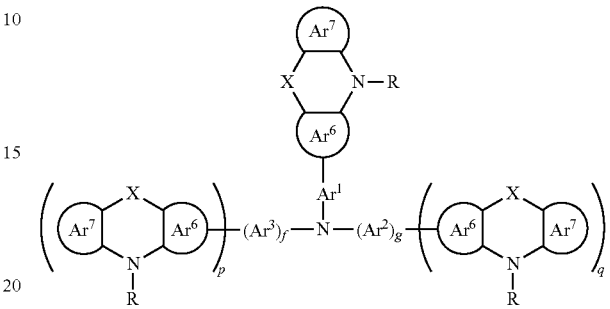

(I)

wherein $Ar^1$, $Ar^2$, $Ar^3$, $Ar^6$ and $Ar^7$ in each occurrence independently represent an unsubstituted or substituted aryl or heteroaryl group; X independently in each occurrence represents S or O; R independently in each occurrence represents H or a substituent; p is 0 or 1; q is 0 or 1; f is 1, 2 or 3; g is 1, 2 or 3; and adjacent groups $Ar^3$ or adjacent groups $Ar^2$ may be linked by a divalent group to form a ring.

Optionally, at least one of p and q is 1.

Optionally, f and g are 1.

Optionally, at least one R is selected from the group consisting of:

alkyl wherein one or more non-adjacent C atoms may be replaced with O, S, substituted N, C=O and —COO— and one or more H atoms of the alkyl group may be replaced with F or aryl or heteroaryl which may be unsubstituted or substituted with one or more substituents; and aryl or heteroaryl which may be unsubstituted or substituted with one or more substituents.

Optionally, R is phenyl which may be unsubstituted or substituted with one or more $C_{1-20}$ alkyl groups.

Optionally, $Ar^1$, $Ar^2$, $Ar^3$, $Ar^6$ and $Ar^7$ are each unsubstituted or substituted phenyl.

Optionally, the compound has formula (II):

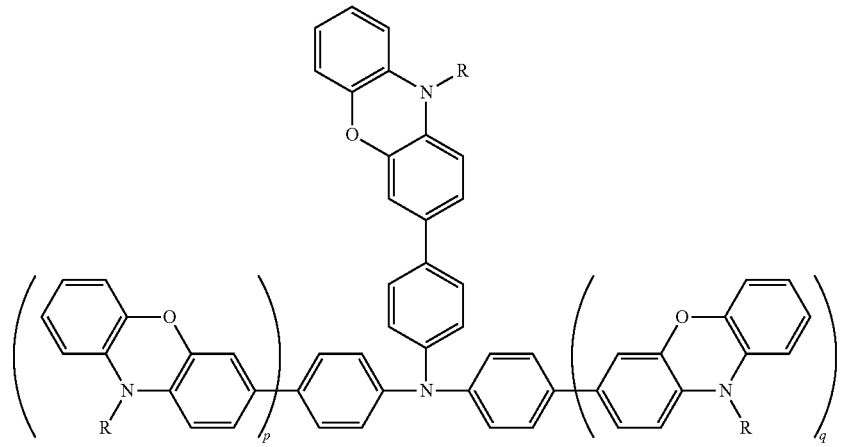

(II)

wherein p, q and R are as defined in any preceding claim.

Optionally, $Ar^1$, $Ar^2$, $Ar^3$, $Ar^6$ and $Ar^7$ in each occurrence is substituted with one or more substituents. Optionally, substituents are selected from the group $R^3$ consisting of:

alkyl, for example $C_{1-20}$ alkyl, wherein one or more non-adjacent C atoms may be replaced with O, S, substituted N, C=O and —COO— and one or more H atoms of the alkyl group may be replaced with F or aryl or heteroaryl which may be unsubstituted or substituted with one or more groups $R^4$, aryl or heteroaryl which may be unsubstituted or substituted with one or more groups $R^4$, $NR^5{}_2$, $OR^5$, $SR^5$, fluorine, nitro and cyano, and crosslinkable groups;

wherein each $R^4$ is independently alkyl, for example $C_{1-20}$ alkyl, in which one or more non-adjacent C atoms may be replaced with O, S, substituted N, C=O and —COO— and one or more H atoms of the alkyl group may be replaced with F, and each $R^5$ is independently selected from the group consisting of alkyl, and aryl or heteroaryl which may be unsubstituted or substituted with one or more alkyl groups.

In one arrangement, one or more groups $Ar^7$ are substituted with one or more substituents, and $Ar^1$, $Ar^2$, $Ar^3$ and $Ar^6$ in each occurrence are unsubstituted.

Substituents for $Ar^1$, $Ar^2$, $Ar^3$, $Ar^6$ and $Ar^7$ are preferably selected from $C_{1-20}$ alkyl.

In a second aspect the invention provides a composition comprising a host material and a dopant comprising a light-emitting compound according to the first aspect.

Optionally according to the second aspect, the host material is a polymer.

Optionally according to the second aspect, the host material is a conjugated polymer.

Optionally, the compound of the first aspect or the composition of the second aspect has a photoluminescent spectrum with a peak wavelength less than 450 nm.

Optionally, the compound of the first aspect or the composition of the second aspect has a CIE(y) co-ordinate in the range of 0.04 to 0.1, optionally in the range 0.04-0.08.

In a third aspect, the invention provides a solution comprising at least one solvent and a compound of the first aspect.

In a fourth aspect, the invention provides an organic light-emitting device comprising an anode, a cathode and a light-emitting layer between the anode and the cathode wherein the light-emitting layer comprises a compound according to the first aspect.

Optionally according to the fourth aspect, the light-emitting layer comprises a composition according to the second aspect.

In a fifth aspect, the invention provides method of forming an organic light-emitting device according to the fourth aspect, the method comprising the step of forming a light emitting layer by depositing a compound according to the first aspect over one of the anode and cathode and depositing the other of the anode and cathode over the light-emitting layer.

Optionally according to the fifth aspect, the light-emitting layer is formed by depositing the solution according to the third aspect and evaporating the solvent.

An advantage of the compounds of the present invention is it can provide a bluer emitter that can be blended into current host formulations (deep blue, CIEy <0.08) suitable for solution processing.

DESCRIPTION OF THE DRAWINGS

The invention will now be described in more detail with reference to the drawings wherein.

DETAILED DESCRIPTION OF THE INVENTION

Figure 1:
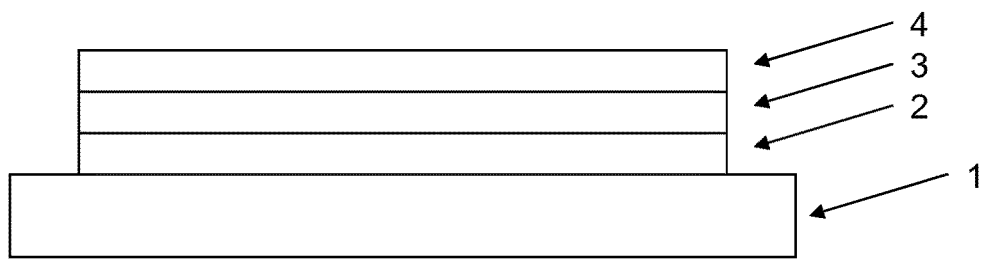
FIG. 1 illustrates an organic light-emitting device according to an embodiment of the invention.

The compound of the invention may be used as a light-emitting and/or hole-transporting material in an OLED. The compound of the invention may be provided in a hole transporting layer and/or in a light-emitting layer.

Where used as a light-emitting compound, it may be a blue light-emitting compound provided in a light-emitting layer of an OLED. The compound may be used alone or in combination with a host material.

Exemplary compounds of the invention include the following, each of which may optionally be substituted with one or more substituents:

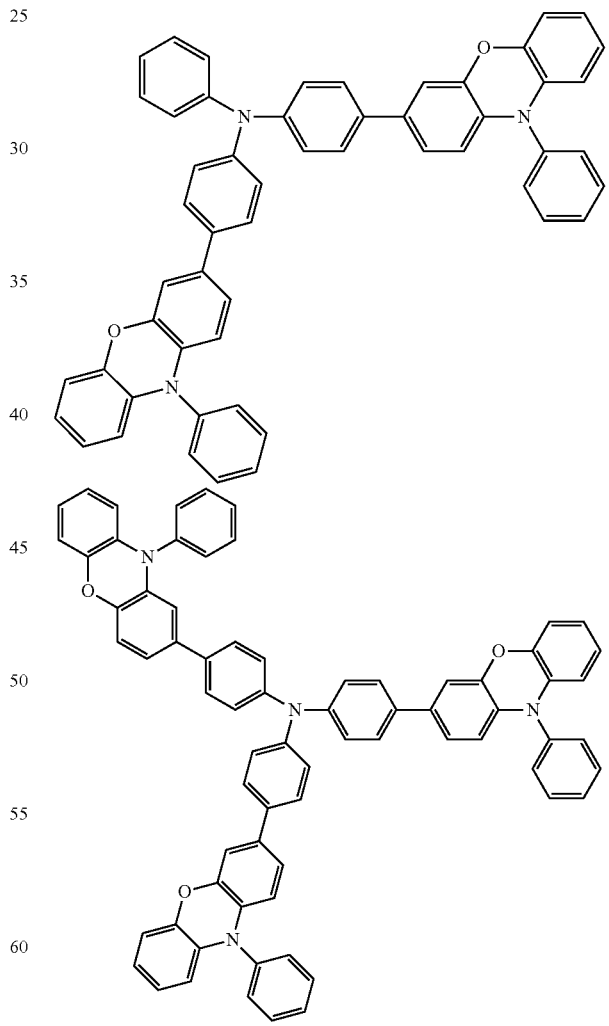

Exemplary substituents for the aromatic groups of the compounds of the invention may be selected from $R^3$ described below with reference to Formula (V). Preferred substituents include $C_{1-20}$ alkyl, and phenyl which may be unsubstituted or substituted with one or more $C_{1-20}$ alkyl groups. Exemplary substituted compounds include the following:
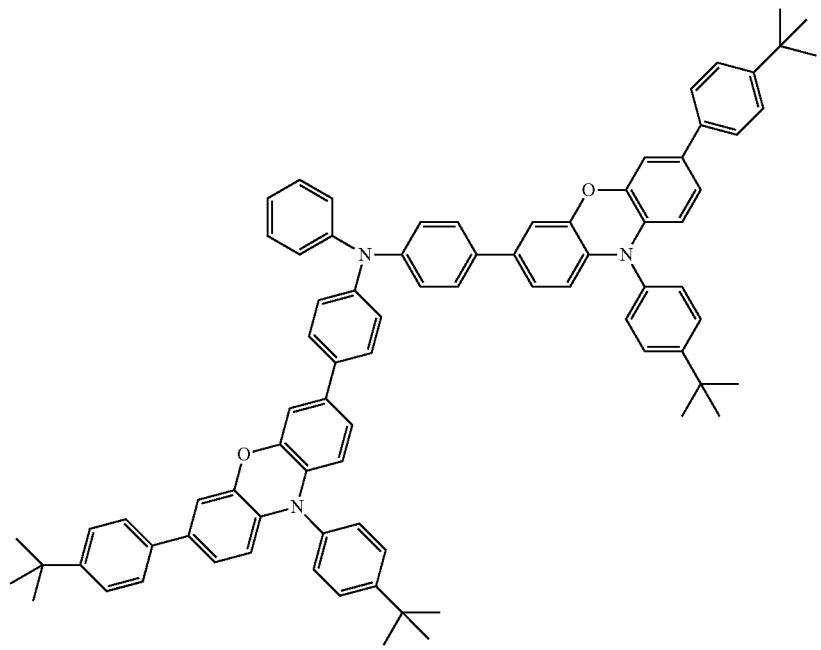
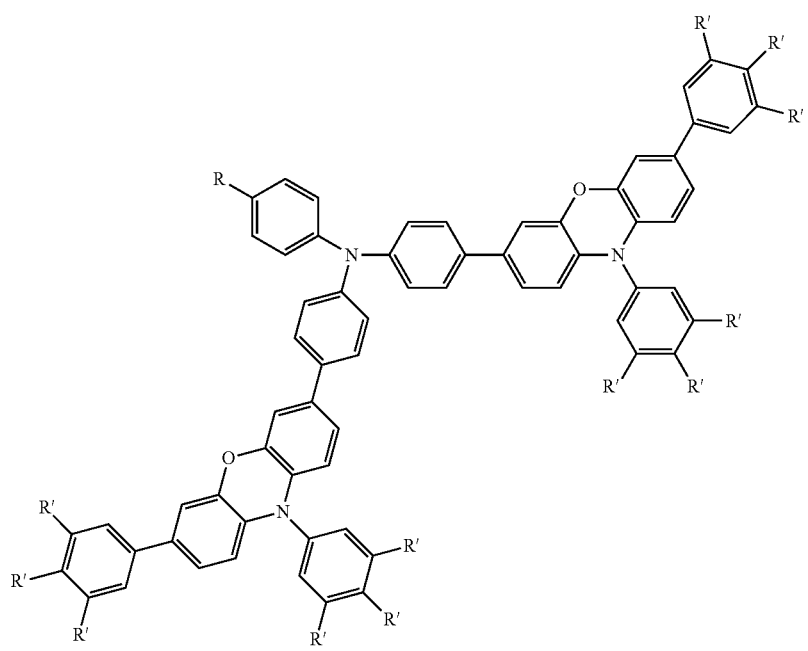

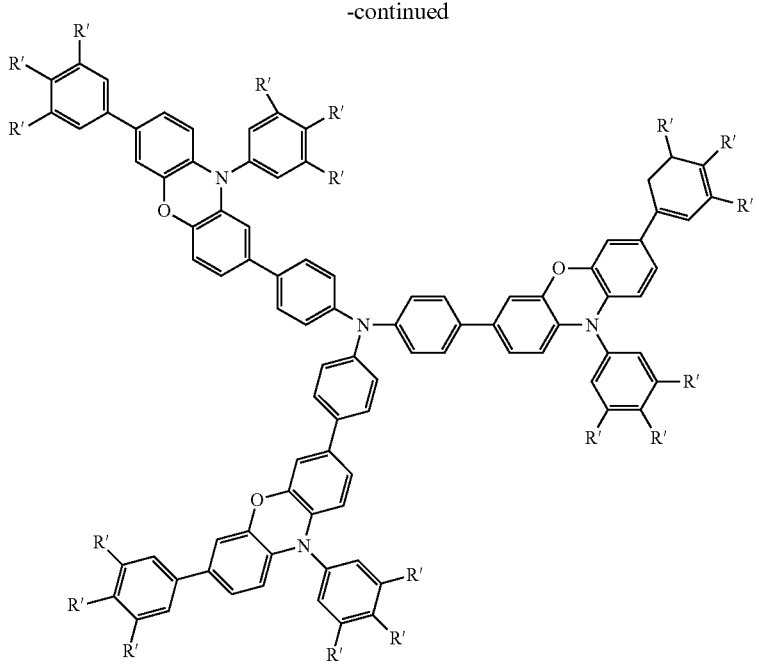

wherein R' in each occurrence independently represents H or $C_{1-20}$ alkyl.

Host Materials

The compound of the invention may be used alone in the light-emitting layer of an OLED, or in combination with one or more materials. The compound may be used with a matrix or host material containing the compound. The compound may be provided in the host or matrix material in an amount in the range of 0.1 mol %-20 mol %, optionally 1-15 mol %.

A host material may be a semiconducting material, for example a polymer. The host polymer may be a homopolymer or copolymer comprising two or more different repeat units. Exemplary semiconducting polymers include conjugated polymers, for example polyarylenes.

In the case of a polymeric host, i.e. a host material having a polydispersity of more than 1, it will be understood that the number of moles of a polymeric repeat unit present in the polymer may be calculated by dividing the weight average molecular weight (Mw) of the polymer by the mean average molecular weight of the polymer's repeat units, and the mol % may be calculated accordingly.

The singlet excited state energy level ($S_1$) of the host material should be higher than that of the compound of the invention in order that singlet excitons may be transferred from the host material to the light-emitting compound. In the case of a conjugated polymer host, the extent of conjugation of the polymer backbone may be selected in order to provide a suitable $S_1$ level of the host. The $S_1$ level of a material may be determined from its photoluminescent spectrum.

Exemplary arylene repeat units are disclosed in for example, Adv. Mater. 2000 12(23) 1737-1750 and include: phenylene repeat units, for example 1,4-linked phenylene repeat units; fluorene repeat units, for example 2,7-linked fluorene repeat units, indenofluorene repeat units and spirobifluorene repeat units.

Phenylene repeat units as disclosed in, for example, J. Appl. Phys. 1996, 79, 934; 2,7-fluorene repeat units are disclosed in, for example, EP 0842208; indenofluorene repeat units as disclosed in, for example, Macromolecules 2000, 33(6), 2016-2020; and spirobifluorene repeat units are disclosed in, for example EP 0707020.

Each of these repeat units is unsubstituted or substituted. Examples of substituents include solubilising groups such as $C_{1-20}$ alkyl or alkoxy; electron withdrawing groups such as fluorine, nitro or cyano; and substituents for increasing glass transition temperature (Tg) of the polymer.

A polyarylene host polymer may comprise only one type of arylene repeat unit, or two or more different arylene repeat units. The arylene repeat units may be provided in an amount of at least 1 mol %, at least 10 mol % or at least 50 mol %. In some embodiments, the polymer may be provided in an amount of more than 50 mol %.

Exemplary fluorene co-repeat units include unsubstituted or substituted 2,7-linked fluorene repeat units, such as repeat units of formula (III):

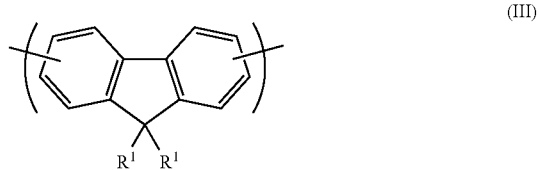

wherein $R^1$ in each occurrence is the same or different and is H or a substituent, and the two groups $R^1$ may be linked to form a ring.

The repeat unit of formula (III) may be linked through the 2- and 7-positions of the fluorene ring for conjugation with adjacent aromatic repeat units. Alternatively, the repeat unit may be linked through other positions, or linked through only one of the 2 and 7 positions, in order to provide less or no conjugation between the repeat unit of formula and any adjacent aromatic repeat units.

$R^1$ is preferably selected from the group consisting of hydrogen; unsubstituted or substituted alkyl wherein one or more non-adjacent C atoms may be replaced with O, S, N, C═O and —COO—; unsubstituted or substituted aryl or heteroaryl, in particular aryl or heteroaryl substituted with one or more alkyl groups, e.g. $C_{1-20}$ alkyl; and unsubstituted or substituted arylalkyl or heteroarylalkyl. More preferably $R^1$ comprises an unsubstituted or substituted alkyl, e.g. $C_1$-$C_{20}$ alkyl, or aryl, in particular phenyl, group.

$R^1$ may comprise a linear or branched chain of aryl or heteroaryl groups, each of which groups may independently be substituted, for example a group of formula $(Ar^3)_r$ as described below with reference to formula (V).

In the case where $R^1$ comprises aryl or heteroaryl, preferred optional substituents include alkyl groups wherein one or more non-adjacent C atoms may be replaced with O, S, N, C═O and —COO—.

$R^1$ may comprise a crosslinkable-group, for example a group comprising a polymerisable double bond such and a vinyl or acrylate group, or a benzocyclobutane group.

One or more of the aromatic carbon atoms of the fluorene unit may be substituted. Optional substituents may be selected from the group consisting of alkyl wherein one or more non-adjacent C atoms may be replaced with O, S, N, C═O and —COO—, unsubstituted or substituted aryl, unsubstituted or substituted heteroaryl, alkoxy, alkylthio, fluorine, cyano and arylalkyl.

Another exemplary class of arylene repeat units is phenylene repeat units, such as phenylene repeat units of formula (IV):

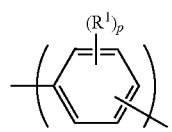

(IV)

wherein p is 0, 1, 2, 3 or 4, optionally 1 or 2, and $R^1$ independently in each occurrence is as described above. The phenylene repeat unit may be 1,2-1,3- or 1,4-linked. In one arrangement, the phenylene repeat unit is 1,4-linked. In another arrangement, the phenylene repeat unit is 1,3-linked. It will be appreciated that the extent of conjugation along a polymer backbone will be reduced in the case of a polymer backbone comprising a 1,3-phenylene repeat unit as compared to a polymer backbone comprising a 1,4-phenylene repeat unit.

A 1,4-phenylene repeat unit may carry substituents $R^1$, e.g. $C_{1-20}$ alkyl, in its 2- and 5-positions. These substituents may cause steric hindrance with adjacent repeat units, causing the repeat unit of formula (IV) to twist out of plane relative to the adjacent repeat units and thereby reducing conjugation along the polymer backbone as compared to an unsubstituted 1,4-phenylene repeat unit A host polymer may comprise arylamine repeat units, for example repeat units of formula (V):

(V)

wherein $Ar^1$ and $Ar^2$ in each occurrence are independently selected from unsubstituted or substituted aryl or heteroaryl groups, z is greater than or equal to 1, preferably 1 or 2, $R^2$ is H or a substituent, preferably a substituent, and x and y are each independently 1, 2 or 3.

The host may be a copolymer comprising one or more arylene repeat units as described above and one or more arylamine repeat units of formula (V).

$R^2$ is preferably alkyl, for example $C_{1-20}$ alkyl, $Ar^3$, or a branched or linear chain of $Ar^3$ groups, for example —$(Ar^3)_r$, wherein $Ar^3$ in each occurrence is independently selected from aryl or heteroaryl and r is at least 1, optionally 1, 2 or 3.

Any of $Ar^1$, $Ar^2$ and $Ar^3$ may independently be substituted with one or more substituents. Preferred substituents are selected from the group $R^3$ consisting of:

alkyl, for example $C_{1-20}$ alkyl, wherein one or more non-adjacent C atoms may be replaced with O, S, substituted N, C═O and —COO— and one or more H atoms of the alkyl group may be replaced with F or aryl or heteroaryl which may be unsubstituted or substituted with one or more groups $R^4$, aryl or heteroaryl which may be unsubstituted or substituted with one or more groups $R^4$, $NR^5_2$, $OR^5$, $SR^5$, fluorine, nitro and cyano, and crosslinkable groups;

wherein each $R^4$ is independently alkyl, for example $C_{1-20}$ alkyl, in which one or more non-adjacent C atoms may be replaced with O, S, substituted N, C═O and —COO— and one or more H atoms of the alkyl group may be replaced with F, and each $R^5$ is independently selected from the group consisting of alkyl and aryl or heteroaryl which may be unsubstituted or substituted with one or more alkyl groups.

$R^2$ may comprise a crosslinkable-group, for example a group comprising a polymerisable double bond such and a vinyl or acrylate group, or a benzocyclobutane group.

Any of the aryl or heteroaryl groups in the repeat unit of Formula (V) may be linked by a direct bond or a divalent linking atom or group. Preferred divalent linking atoms and groups include O, S; substituted N; and substituted C.

Where present, substituted N or substituted C of $R^3$, $R^4$ or of the divalent linking group may independently in each occurrence be $NR^6$ or $CR^6_2$ respectively wherein $R^6$ is alkyl or unsubstituted or substituted aryl or heteroaryl. Optional substituents for aryl or heteroaryl groups $R^6$ may be selected from $R^4$ or $R^5$.

In one preferred arrangement, $R^2$ is $Ar^3$ and each of $Ar^1$, $Ar^2$ and $Ar^3$ are independently unsubstituted or substituted with one or more $C_{1-20}$ alkyl groups.

Particularly preferred units satisfying Formula (V) include units of Formulae 1-3:

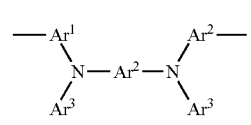

1

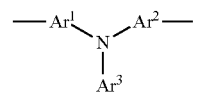

2

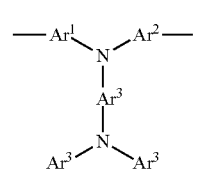

3 wherein $Ar^1$ and $Ar^2$ are as defined above; and $Ar^3$ is unsubstituted or substituted aryl or heteroaryl. Where present, preferred substituents for $Ar^3$ include substituents as described for $Ar^1$ and $Ar^2$, in particular alkyl and alkoxy groups.

$Ar^1$, $Ar^2$ and $Ar^3$ are preferably phenyl, each of which may independently be substituted with one or more substituents as described above.

In another preferred arrangement, aryl or heteroaryl groups of formula (V) are phenyl, each phenyl group being unsubstituted or substituted with one or more alkyl groups.

In another preferred arrangement, $Ar^1$, $Ar^2$ and $Ar^3$ are phenyl, each of which may be substituted with one or more $C_{1-20}$ alkyl groups, and r=1.

In another preferred arrangement, $Ar^1$ and $Ar^2$ are phenyl, each of which may be substituted with one or more $C_{1-20}$ alkyl groups, and $R^2$ is 3,5-diphenylbenzene wherein each phenyl may be substituted with one or more alkyl groups.

Arylamine repeat units may be provided in an amount of at least 1 mol %, optionally at least 5 mol %.

The polymer may comprise non-conjugating repeat units, i.e. units that break conjugation between repeat units on either side of the non-conjugating repeat units. Exemplary non-conjugating repeat units have the following formula:

$$-Ar^1-(CH_2)_d-Ar^2-$$

wherein $Ar^1$ and $Ar^2$, which may be the same or different, are each unsubstituted or substituted aryl or heteroaryl as described above, for example phenyl substituted with one or more $C_{1-20}$ alkyl groups, and d is at least 1, optionally an integer from 1-10.

One or more non-adjacent C atoms of $-(CH_2)_d-$ may be replaced with O, S, substituted N, C=O and —COO— and one or more H atoms of the alkyl group may be replaced with F or $C_{1-10}$ alkyl.

Polymer Synthesis

Preferred methods for preparation of conjugated polymers comprise a "metal insertion" wherein the metal atom of a metal complex catalyst is inserted between an aryl or heteroaryl group and a leaving group of a monomer. Exemplary metal insertion methods are Suzuki polymerisation as described in, for example, WO 00/53656 and Yamamoto polymerisation as described in, for example, T. Yamamoto, "Electrically Conducting And Thermally Stable pi-Conjugated Poly(arylene)s Prepared by Organometallic Processes", Progress in Polymer Science 1993, 17, 1153-1205. In the case of Yamamoto polymerisation, a nickel complex catalyst is used; in the case of Suzuki polymerisation, a palladium complex catalyst is used.

For example, in the synthesis of a linear polymer by Yamamoto polymerisation, a monomer having two reactive halogen groups may be used. Similarly, according to the method of Suzuki polymerisation, at least one reactive group is a boron derivative group such as a boronic acid or boronic ester and the other reactive group is a halogen. Preferred halogens are chlorine, bromine and iodine, most preferably bromine.

It will therefore be appreciated that repeat units illustrated throughout this application may be derived from a monomer carrying suitable leaving groups. Likewise, an end group or side group may be bound to the polymer by reaction of a suitable leaving group.

Suzuki polymerisation may be used to prepare regioregular, block and random copolymers. In particular, homopolymers or random copolymers may be prepared when one reactive group is a halogen and the other reactive group is a boron derivative group. Alternatively, block or regioregular copolymers may be prepared when both reactive groups of a first monomer are boron and both reactive groups of a second monomer are halogen.

As alternatives to halides, other leaving groups capable of participating in metal insertion include sulfonic acids and sulfonic acid esters such as tosylate, mesylate and triflate.

Device Structure

With reference to FIG. 1, an organic light-emitting device according to an embodiment of the invention comprises an anode 2, for example indium tin oxide, supported on a substrate 1, a light-emitting layer 3 comprising a compound according to the invention and a cathode 4. One or more further layers may be provided between the anode and cathode, for example hole injection and/or hole transporting layers as described in more detail below, or one or more further light-emitting layers.

The device may be, without limitation, a display, for example a full-colour display, or a white light-emitting device.

Light-Emitting Layer

The compound of the invention may be provided as a light-emitting compound, for example a blue light-emitting compound, in the light-emitting layer 3.

The light-emitting layer may consist of a light-emitting material alone, or may comprise this material in combination with one or more further materials. In particular, the light-emitting material may be blended with a host material.

More than one light-emitting material may be used. For example, red, green and blue light-emitting materials may be used to obtain white light emission. These different light-emitting materials may be in the same or in different light-emitting layers.

A green light-emitting material may have photoluminescent spectrum with a peak wavelength in the range of above 480 nm-560 nm.

A red light-emitting material may have photoluminescent spectrum with a peak wavelength in the range of above 560 nm-630 nm.

The light-emitting layer may include one or more phosphorescent materials, for example phosphorescent dopants doped into a host material. If a host material is used for the compound according to the invention then it may be the same as or different to the host for phosphorescent materials in the light-emitting layer.

The triplet excited state ($T_1$) level of the host material should be higher than that of any phosphorescent dopant it is used with.

Exemplary phosphorescent light-emitting dopants include metal complexes comprising unsubstituted or substituted complexes of formula (VI):

$$ML^1_{q'}L^2_{r'}L^3_{s'} \quad (VI)$$

wherein M is a metal; each of $L^1$, $L^2$ and $L^3$ is a coordinating group; q' is an integer; r' and s' are each independently 0 or an integer; and the sum of (a. q')+(b. r')+(c.s') is equal to the number of coordination sites available on M, wherein a is the number of coordination sites on $L^1$, b is the number of coordination sites on $L^2$ and c is the number of coordination sites on $L^3$.

Heavy elements M induce strong spin-orbit coupling to allow rapid intersystem crossing and emission from triplet or higher states (phosphorescence). Suitable heavy metals M include d-block metals, in particular those in rows 2 and 3 i.e. elements 39 to 48 and 72 to 80, in particular ruthenium, rhodium, palladium, rhenium, osmium, iridium, platinum and gold. Iridium are particularly preferred.

Exemplary ligands $L^1$, $L^2$ and $L^3$ include carbon or nitrogen donors such as porphyrin or bidentate ligands of formula (VII):

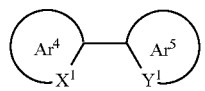

(VII)

wherein $Ar^4$ and $Ar^5$ may be the same or different and are independently selected from unsubstituted or substituted aryl or heteroaryl; $X^1$ and $Y^1$ may be the same or different and are independently selected from carbon or nitrogen; and $Ar^4$ and $Ar^5$ may be fused together. Ligands wherein $X^1$ is carbon and $Y^1$ is nitrogen are particularly preferred.

Examples of bidentate ligands are illustrated below:

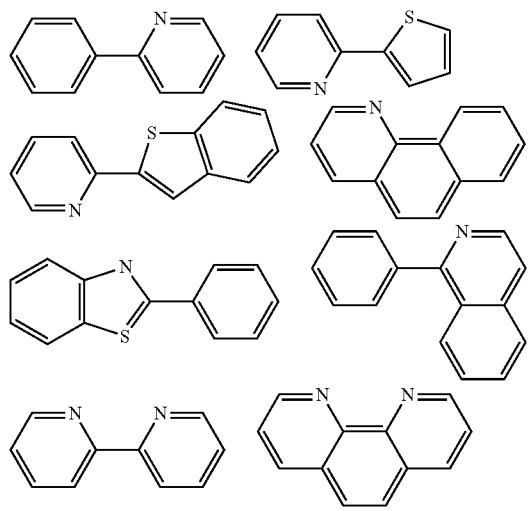

Each of $Ar^4$ and $Ar^5$ may carry one or more substituents. Two or more of these substituents may be linked to form a ring, for example an aromatic ring.

Other ligands suitable for use with d-block elements include diketonates, in particular acetylacetonate (acac); triarylphosphines and pyridine, each of which may be substituted.

Exemplary substituents include groups $R^3$ as described above with reference to Formula (V). Particularly preferred substituents include fluorine or trifluoromethyl which may be used to blue-shift the emission of the complex, for example as disclosed in WO 02/45466, WO 02/44189, US 2002-117662 and US 2002-182441; alkyl or alkoxy groups, for example $C_{1-20}$ alkyl or alkoxy, which may be as disclosed in JP 2002-324679; carbazole which may be used to assist hole transport to the complex when used as an emissive material, for example as disclosed in WO 02/81448; bromine, chlorine or iodine which can serve to functionalise the ligand for attachment of further groups, for example as disclosed in WO 02/68435 and EP 1245659; and dendrons which may be used to obtain or enhance solution processability of the metal complex, for example as disclosed in WO 02/66552.

A light-emitting dendrimer typically comprises a light-emitting core bound to one or more dendrons, wherein each dendron comprises a branching point and two or more dendritic branches. Preferably, the dendron is at least partially conjugated, and at least one of the branching points and dendritic branches comprises an aryl or heteroaryl group, for example a phenyl group. In one arrangement, the branching point group and the branching groups are all phenyl, and each phenyl may independently be substituted with one or more substituents, for example alkyl or alkoxy.

A dendron may have unsubstituted or substituted formula (VIII):

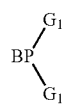

(VIII)

wherein BP represents a branching point for attachment to a core and $G_1$ represents first generation branching groups.

The dendron may be a first, second, third or higher generation dendron. $G_1$ may be substituted with two or more second generation branching groups $G_2$, and so on, as in unsubstituted or substituted formula (VIIIa):

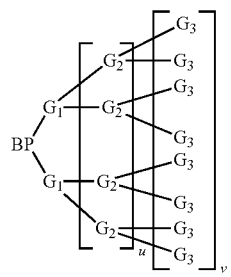

(VIIIa)

wherein u is 0 or 1; v is 0 if u is 0 or may be 0 or 1 if u is 1; BP represents a branching point for attachment to a core and $G_1$, $G_2$ and $G_3$ represent first, second and third generation dendron branching groups.

BP and/or any group G may be substituted with one or more substituents, for example one or more $C_{1-20}$ alkyl or alkoxy groups.

Where used, a light-emitting dopant may be present in an amount of about 0.05 mol % up to about 20 mol %, optionally about 0.1-10 mol % relative to their host material.

The light-emitting dopant may be physically mixed with the host material or it may be chemically bound to the host material in the same manner described above with respect to binding of the light-emitting dopant to the charge transporting material.

A host polymer as described above may be used as a host for blue emission from the inventive compound, and from one or more phosphorescent dopants such as a red or green phosphorescent dopant.

The material of the invention may itself be used as a host for a fluorescent or phosphorescent dopant, for example it may be used as a host for a red phosphorescent material.

More than one light-emitting layer may be present.

The light-emitting layer(s) may be patterned or unpatterned. A device comprising an unpatterned layer may be used an illumination source, for example. A white light emitting device is particularly suitable for this purpose. A device comprising a patterned layer may be, for example, an active matrix display or a passive matrix display. In the case of an active matrix display, a patterned electroluminescent layer is typically used in combination with a patterned anode layer and an unpatterned cathode. In the case of a passive matrix display, the anode layer is formed of parallel stripes of anode material, and parallel stripes of electroluminescent material and cathode material arranged perpendicular to the anode material wherein the stripes of electroluminescent material and cathode material are typically separated by stripes of insulating material ("cathode separators") formed by photolithography.

Cathode

Cathode 4 may be selected from materials that have a workfunction allowing injection of electrons into the light-emitting layer. Other factors influence the selection of the cathode such as the possibility of adverse chemical reactions between the cathode and the materials of the light-emitting layer or other layer adjacent to the cathode. The cathode may consist of a single layer of a conductive material such as a layer of a metal, e.g. aluminium. Alternatively, it may comprise a plurality of materials, for example a bilayer of a low workfunction material and a high workfunction material such as calcium and aluminium as disclosed in WO 98/10621; elemental barium as disclosed in WO 98/57381, Appl. Phys. Lett. 2002, 81(4), 634 and WO 02/84759; or a thin layer of metal compound, in particular an oxide or fluoride of an alkali or alkali earth metal, to assist electron injection, for example lithium fluoride as disclosed in WO 00/48258; barium fluoride as disclosed in Appl. Phys. Lett. 2001, 79(5), 2001; and barium oxide. In order to provide efficient injection of electrons into the device, the cathode preferably has a workfunction of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode will comprise a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

In one arrangement, the surface of the cathode contacts a surface of the light-emitting layer. In another arrangement, one or more layers may be provided between the cathode and the light-emitting layer. For example, an organic electron-transporting layer may be provided between the light-emitting layer and the cathode.

Hole Injection Layers

A conductive hole injection layer, which may be formed from a conductive organic or inorganic material, may be provided between the anode 2 and the light-emitting layer 3 to assist hole injection from the anode into the layer or layers of semiconducting polymer. Examples of doped organic hole injection materials include unsubstituted or substituted, doped poly(ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion ®; polyaniline as disclosed in U.S. Pat. Nos. 5,723,873 and 5,798,170; and unsubstituted or substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Charge Transporting Layers

A hole transporting layer may be provided between the anode 2 and the light-emitting layer 3. Likewise, an electron transporting layer may be provided between the cathode 4 and the light-emitting layer 3.

Similarly, an electron blocking layer may be provided between the anode 2 and the light-emitting layer 3 and a hole blocking layer may be provided between the cathode 4 and the light-emitting layer 3. Transporting and blocking layers may be used in combination. Depending on its HOMO and LUMO levels, a single layer may both transport one of holes and electrons and block the other of holes and electrons.

If present, a hole transporting layer located between anode 2 and light-emitting layer 3 preferably has a HOMO level of less than or equal to 5.5 eV, more preferably around 4.8-5.5 eV. HOMO levels may be measured by cyclic voltammetry.

If present, an electron transporting layer located between light-emitting layer 3 and cathode 4 preferably has a LUMO level of around 3-3.5 eV as measured by cyclic voltammetry. For example, a layer of a silicon monoxide or silicon dioxide or other thin dielectric layer having thickness in the range of 0.2-2 nm may be provided between light-emitting layer 3 and layer 4.

A hole-transporting polymer may comprise arylamine repeat units, in particular repeat units of formula (V). This polymer may be a homopolymer or it may be a copolymer comprising arylene co-repeat units, for example repeat units of formula (III).

Charge transporting units may be provided in a polymer main-chain or polymer side-chain.

Encapsulation

OLEDs tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise a plastic as in U.S. Pat. No. 6,268,695 which discloses a substrate of alternating plastic and barrier layers or a laminate of thin glass and plastic as disclosed in EP 0949850. The substrate may be opaque in the case of an OLED with a transparent cathode.

The device is preferably encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric as disclosed in, for example, WO 01/81649 or an airtight container as disclosed in, for example, WO 01/19142. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Solution Processing

A layer containing the compound of the invention may be formed by depositing a solution of the compound in one or more solvents followed by evaporation of the solvent. The solution may consist essentially of the inventive compound and one or more solvents. Alternatively, one or more further materials may be present, for example a host material.

Solution deposition methods include coating techniques, such as spin-coating, dip-coating and blade coating and printing techniques such as inkjet printing, screen printing and roll printing.

Coating methods such as spin-coating are particularly suitable for devices wherein patterning of the electroluminescent material is unnecessary—for example for lighting applications or simple monochrome segmented displays.

Printing techniques, for example inkjet printing, are particularly suitable for high information content displays, in particular full colour displays. A device may be inkjet printed by providing a patterned layer over a first electrode, typically the anode, and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

If multiple layers of an OLED are formed by solution processing then techniques to prevent intermixing of adjacent layers include crosslinking of one layer before deposition of a subsequent layer and / or selection of materials for adjacent layers such that the material from which the first of these layers is formed is not soluble in the solvent used to deposit the second layer. For example, a hole-transporting layer formed by depositing a hole-transporting material from a solution in a solvent may be crosslinked prior to solution deposition of a light-emitting material to form a light-emitting layer. Crosslinking may be thermal or photo-crosslinking.

EXAMPLES

Compound Example 1

Compound 1 was prepared according to the following method:

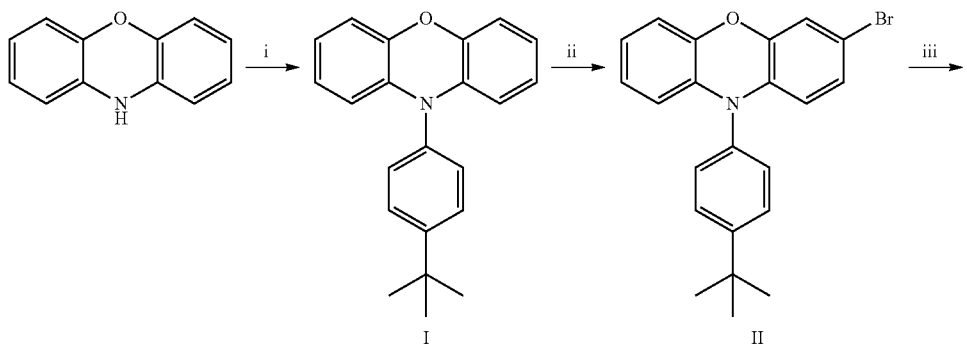

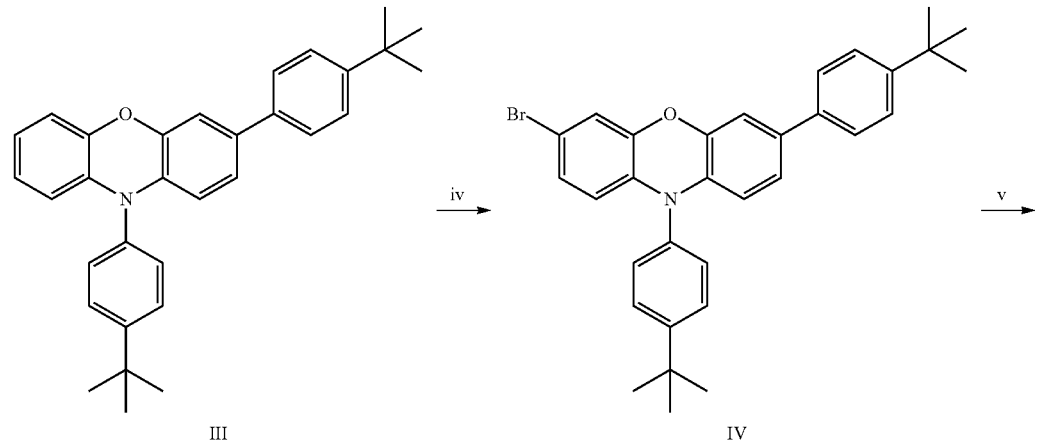

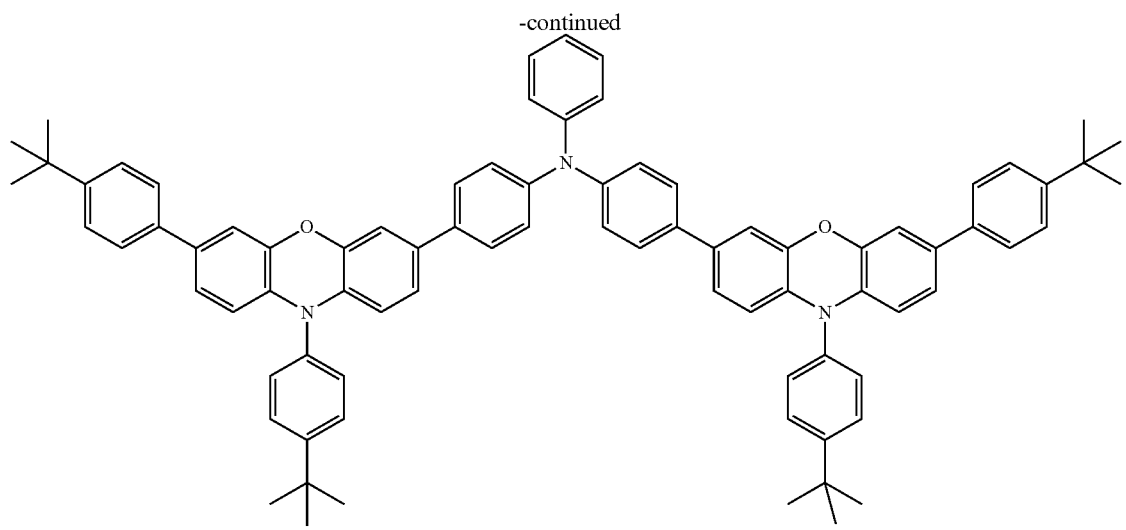

Compound 1 i. 1-Bromo-4-tert-butylbenzene, toluene, PdO(Ac)₂, P(o-tol)₃, sodium tert-pendoxide, 130° C., 20 hrs
ii. 1,3-Dibromo-5,5-dimethyl hydantoin, DCM, DMF, -5° C. to RT, 20 hrs
iii. 4-Tert-butylphenylboronic acid, toluene, PdOAc₂, P(PhOMe)₃, Et₄NOH, 115° C., 20 hrs
iv. 1,3-Dibromo-5,5-dimethyl hydantoin, DCM, DMF, -5° C. to RT, 20 hrs
v. 4′-Diboronic acid pinacol ester triphenylamine, toluene, Pd(OAc)₂, P(PhOMe)₃, bis(tetraethylammonium) carbonate, 115° C., 20 hrs Intermediate I: A solution of phenoxazine (156.28 g, 0.85 mol, 1.1 eq)) and 1-bromo-4-tert-butylbenzene (165.26 g, 0.78 mol, 1.0 eq) in toluene (2 L) was degassed by bubbling nitrogen through the reaction mixture for 1 hour. Palladium acetate (3.5 g, 15.5 mmol, 0.02 eq) and tri(o-tolyl)phosphine (4.72 g, 15.5 mmol, 0.02 eq) were added and the solution stirred for a further 30 mins at RT. After this time sodium tert-pentoxide (170.81 g, 1.55 mol, 2.0 eq) was added and stirring continued for an additional 30 mins at ambient temperature before stirring at 130° C. overnight. The reaction mixture was then cooled in an ice-water bath and quenched by the addition of water (500 ml) and filtered though a celite-florisil plug. Concentration under reduced pressure followed by titration (twice with hot MeCN) and drying under vacuum at 40° C., gave the product as a grey solid (149 g, 82%). GCMS: M+315 (100%).

Intermediate II: A solution of Intermediate I (98.56 g, 0.31 mol) in anhydrous DCM (2 L) under N2, was cooled to −5° C. (internal temperature) using a ice/water bath. 1,3-Dibromo-5,5-dimethyl hydantoin (49.2 g, 0.17 mol) was transferred to a 500 ml round bottom flask and flushed with nitrogen for 15 mins. Anhydrous DMF (100 ml) was then added and the solution transferred via cannular to a dropping funnel. This solution was added dropwise to the reaction mixture, so as to maintain a temperature between 0 and −5° C., and the reaction mixture was allowed to warm to room temperature overnight. The resulting green suspension was filtered through an alumina plug using DCM as eluant. Concentration under reduced pressure followed by titration (twice with MeCN) and drying under vacuum at 40° C., gave the product as a beige solid (84.7 g, 68%). GCMS: GCMS: M+394 (96%).

Intermediate III: A solution of intermediate II (112.00 g, 0.28 mol, 1.0 eq)) and 4-tert-butylphenylboronic acid (55.61 g, 0.31 mol, 1.1 eq) in toluene (1.5 L) was degassed by bubbling nitrogen through the reaction mixture for 1 hour. Palladium acetate (1.5 g, 28.4 mmol, 0.01 eq) and tris(o-methoxyphenyl)phosphine (4.00 g, 11.4 mmol, 0.04 eq) were added, followed by addition of tetraethyl ammonium hydroxide (500 ml, 20 wt % in water) quickly, over 20 mins. After stirring overnight at 115° C., the solution was cooled to room temperature, the base separated and the reaction mixture filtered through a silica gel plug. Concentration under reduced pressure followed by titration (several times with IPA), filtration and drying under vacuum at 40° C., gave the product as a beige solid (90 g, 93%). GCMS: M+448 (94%).

Intermediate IV: A solution of Intermediate III (89.9, 0.20 mol) in anhydrous DCM (1.6 L) under N₂, was cooled to −5° C. (internal temperature) using a ice/water bath. 1,3-Dibromo-5,5-dimethyl hydantoin (31.5 g, 0.11 mol) was transferred to a 250 ml round bottom flask and flushed with nitrogen for 15 mins. Anhydrous DMF (80 ml) was then added and the solution transferred via cannular to a dropping funnel. This solution was added dropwise to the reaction mixture, so as to maintain a temperature between 0 and −5° C. and the reaction mixture was allowed to warm to room temperature overnight. The resulting green solution was filtered through an alumina plug using DCM as eluant. Concentration under reduced pressure followed by titration (twice from MeCN) and drying under vacuum at 40° C., gave the product as a beige solid (91 g, 86%). GCMS: M+448 (94%).

Compound I: A solution of intermediate IV (10.00 g, 19.0 mmol, 2.1 eq) and 4,4′-diboronic acid pinacol ester triphenylamine (4.48 g, 9.0 mmol, 1.0 eq) in toluene (100 ml) was degassed by bubbling nitrogen through the reaction mixture for 1 hour. Palladium acetate (0.02 g, 0.09 mmol, 0.01 eq) and tris(o-methoxyphenyl)

phosphine (0.13 g, 0.37 mmol, 0.04 eq) were added, followed by addition of bis(tetraethylammonium)carbonate (50 ml, 35 wt % in water) quickly over 20 mins. After stirring overnight at 115° C., the solution was cooled to room temperature, the base separated and the reaction mixture filtered through a silica gel-fluorsil plug eluting with DCM. The resulting crude solid was purified by repeated column chromatography (silica-gel, 20% DCM/hexane) and recrystalization from DCM/hexane until the desired purity of >99.6% (HPLC) was achieved. The resulting material was dried under vacuum at 40° C., to give the product as a bright yellow solid.

Compound 2

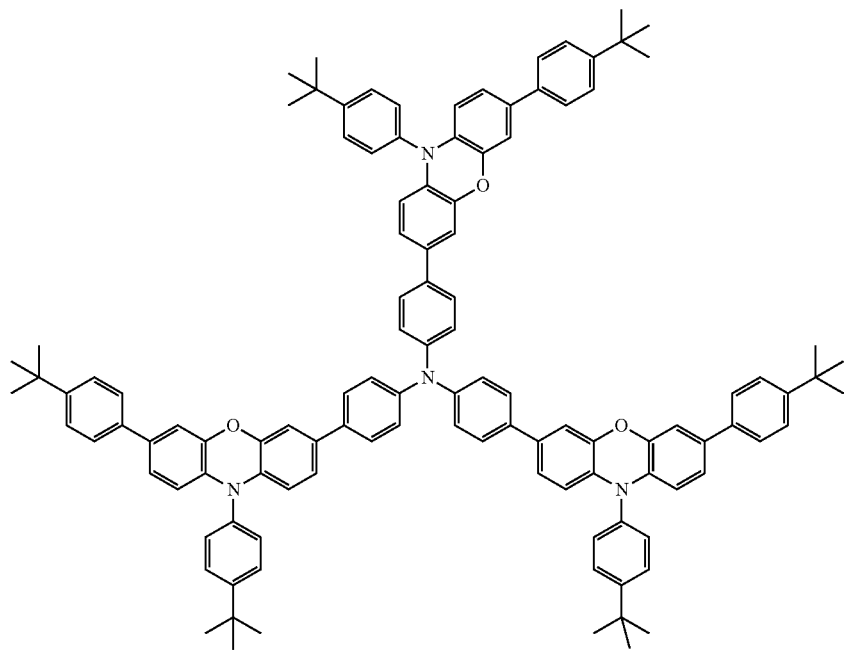

Compound 2: A solution of intermediate IV (2.0 g, 3.8 mmol, 3.2 eq) and 4,4'-diboronic acid pinacol ester triphenylamine (0.74 g, 1.2 mmol, 1.0 eq) in toluene (20 ml) was degassed by bubbling nitrogen through the reaction mixture for 1 hour. Palladium acetate (3 mg, 0.01 mmol, 0.01 eq) and tris(o-methoxyphenyl)phosphine (16 mg, 0.05 mmol, 0.04 eq) were added, followed by addition of bis(tetraethylammonium) carbonate (10 ml, 35 wt % in water) quickly over 20 mins. After stirring overnight at 115° C., the solution was cooled to room temperature, the base separated and the reaction mixture filtered through a silica gel-fluorsil plug eluting with DCM. The resulting crude solid was purified by repeated column chromatography (silica-gel, 20% DCM/hexane) and recrystalization from DCM/hexane until the desired purity of >99.6% (HPLC) was achieved. The resulting material was dried under vacuum at 40° C., to give the product as a bright yellow solid.

Figure 2:
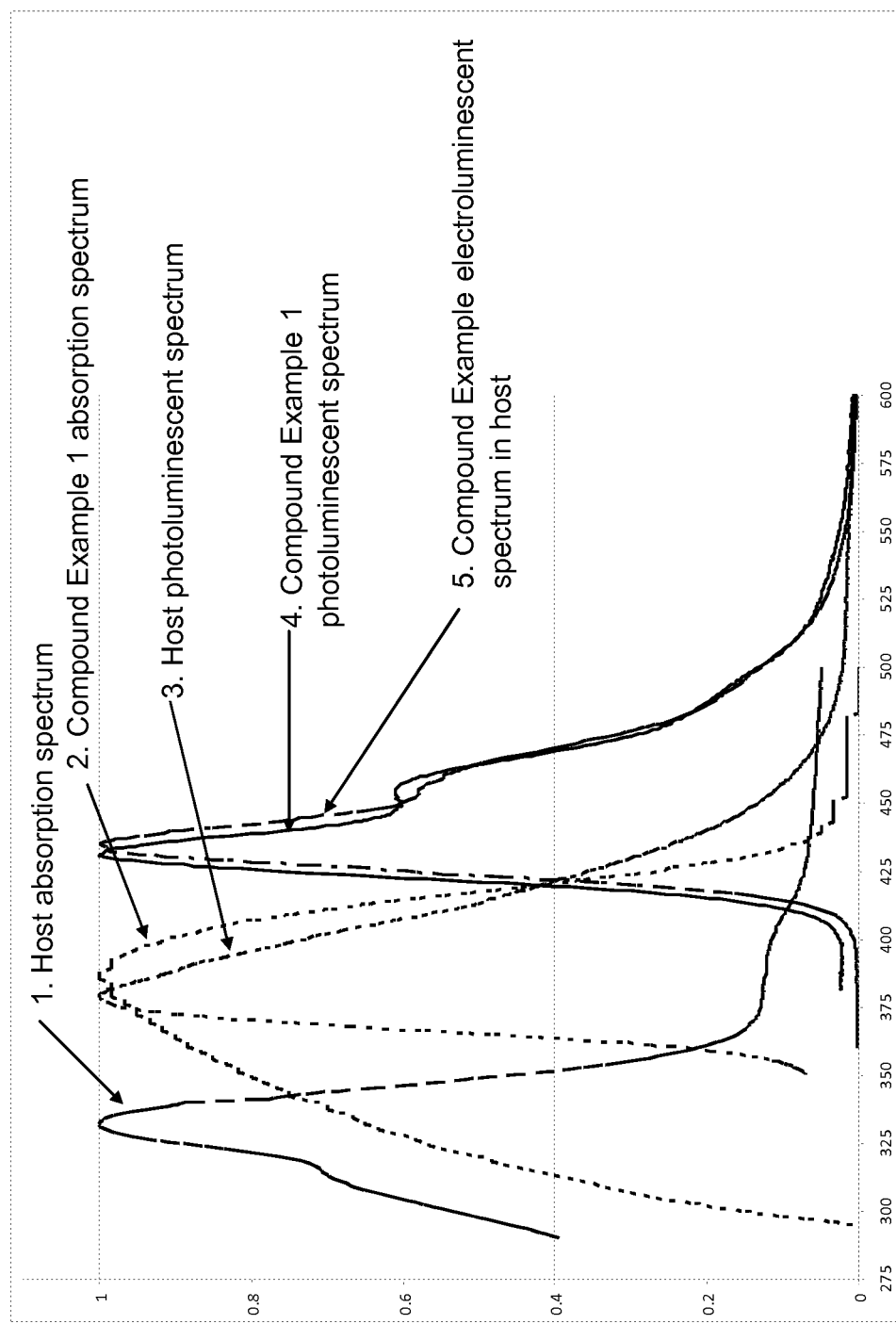
FIG. 2 illustrates photoluminescent and absorption spectra of a light-emitting material according to an example of the invention and a host for this light-emitting material, and the electroluminescent spectrum of an OLED comprising the exemplary light-emitting material in the host.

FIG. 2 illustrates the photoluminescent and UV absorption spectra of Compound Example 1 and host material for Compound Example 1. The host material is a polymer containing the following two repeat units present in an amount of 50 mol % each:

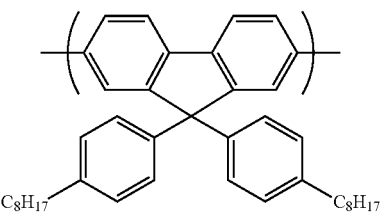

Compound 2

-continued

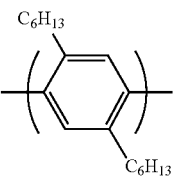

The photoluminescence spectrum of Compound Example 1 shows that it is a blue light-emitting material with a peak at about 430 nm.

Device Example 1

A device having the following structure was prepared: Anode/HIL/HTL/LEL/Cathode
wherein the anode was formed from indium-tin oxide; HIL is a hole injection layer formed by spin-coating a hole-injection material available from Plextronics Inc., HTL is a hole-transporting polymer; LEL is a light-emitting layer formed by spin-coating a solution comprising Compound Example 1 and the host polymer described above; and the cathode comprises a first layer of a metal fluoride and a second layer of aluminium.

FIG. 2 illustrates that the electroluminescence spectrum of this device.is very similar to the photoluminescence spectrum of Compound Example 1, indicating that emission is from Compound Example 1.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. An organic light-emitting device comprising an anode, a cathode and a light-emitting layer between the anode and the cathode wherein the light-emitting layer comprises a compound of formula (I):

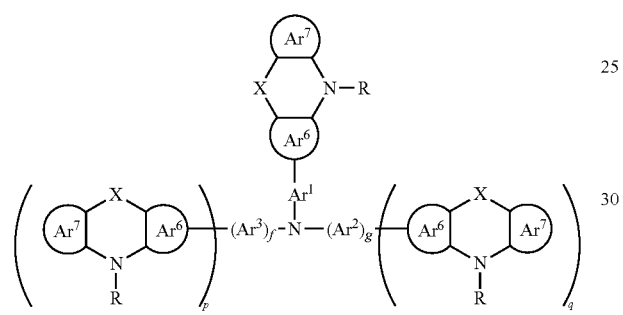

(I)

wherein $Ar^1$, $Ar^2$, $Ar^3$, $Ar^6$ and $Ar^7$ in each occurrence independently represent an unsubstituted or substituted phenyl; X independently in each occurrence represents O; R independently in each occurrence represents H or a substituent; p is 0 or 1; q is 0 or 1; at least one of p and q is 1; f is 1, 2 or 3; g is 1, 2 or 3; and adjacent groups $Ar^3$ or adjacent groups $Ar^2$ may be linked by a divalent group to form a ring.

2. An organic light-emitting device according to claim 1 wherein f and g are 1.

3. An organic light-emitting device according to claim 1 wherein at least one R is selected from the group consisting of:
alkyl wherein one or more non-adjacent C atoms may be replaced with O, S, substituted N, C=O and —COO— and one or more H atoms of the alkyl group may be replaced with F or aryl or heteroaryl which may be unsubstituted or substituted with one or more substituents; and
aryl or heteroaryl which may be unsubstituted or substituted with one or more substituents.

4. An organic light-emitting device according to claim 3 wherein R is phenyl which may be unsubstituted or substituted with one or more $C_{1-20}$ alkyl groups.

5. An organic light-emitting device according to claim 1 wherein $Ar^1$, $Ar^2$, $Ar^3$, $Ar^6$ and $Ar^7$ in each occurrence is unsubstituted or substituted with one or more substituents selected from the group consisting of alkyl wherein one or more non-adjacent C atoms may be replaced with O, S, substituted N, C=O and —COO— and one or more H atoms of the alkyl group may be replaced with F.

6. An organic light-emitting device wherein the light-emitting layer comprises a host material and a dopant, the dopant comprising a light-emitting compound according to formula (I)

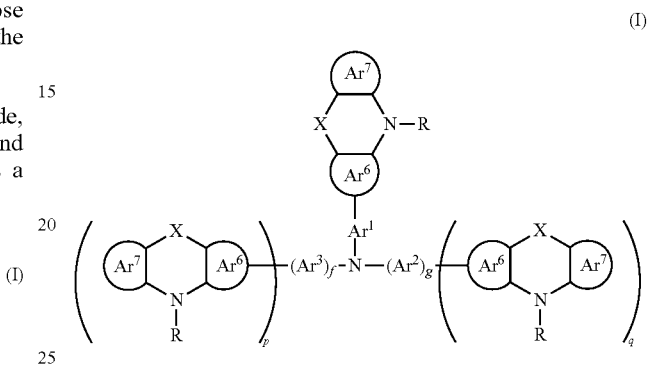

(I)

wherein $Ar^1$, $Ar^2$, $Ar^3$, $Ar^6$ and $Ar^7$ in each occurrence independently represent an unsubstituted or substituted phenyl; X independently in each occurrence represents O; R independently in each occurrence represents H or a substituent; p is 0 or 1; q is 0 or 1; at least one of p and q is 1; f is 1, 2 or 3; g is 1, 2 or 3; and adjacent groups $Ar^3$ or adjacent groups $Ar^2$ may be linked by a divalent group to form a ring.

7. An organic light-emitting device according to claim 6 wherein the host material is a polymer.

8. An organic light-emitting device according to claim 7 wherein the host material is a conjugated polymer.

9. An organic light-emitting device according to claim 1 wherein the compound according to formula (I) has a photoluminescent spectrum with a peak wavelength less than 450 nm.

10. An organic light-emitting device according to claim 1 wherein the compound according to formula (I) has a CIE(y) co-ordinate in the range of 0.04 to 0.1.

11. A method of forming an organic light-emitting device according to claim 1 comprising the step of forming the light-emitting layer by depositing a compound according to formula (I) over one of the anode and cathode and depositing the other of the anode and cathode over the light-emitting layer.

12. A method according to claim 11 wherein the light-emitting layer is formed by depositing a solution comprising at least one solvent and a compound according to formula (I) and evaporating the solvent.

13. An organic light-emitting device according to claim 1 further comprising a conductive hole injection layer between the anode and the light-emitting layer.

* * * * *